United States Patent [19]

Manner et al.

[11] Patent Number: 5,371,264
[45] Date of Patent: Dec. 6, 1994

[54] PROCESS FOR PREPARING N,O-DISUBSTITUTED HYDROXYLAMINE COMPOUNDS

[75] Inventors: James A. Manner, Monroeville; Suresh B. Damle, Pittsburgh, both of Pa.

[73] Assignee: PPG Industries, Inc., Pittsburgh, Pa.

[21] Appl. No.: 9,528

[22] Filed: Jan. 27, 1993

[51] Int. Cl.$^5$ .............................................. C07C 69/96
[52] U.S. Cl. .................. 558/260; 558/262; 562/874
[58] Field of Search .......................... 558/262; 562/874

[56] References Cited

U.S. PATENT DOCUMENTS

| | | | |
|---|---|---|---|
| 3,192,261 | 6/1965 | Losee et al. | 562/874 |
| 3,371,106 | 2/1968 | Berliner et al. | 562/874 |
| 4,873,259 | 10/1989 | Summers, Jr. et al. | 514/443 |

OTHER PUBLICATIONS

Chemical Abstracts, vol. 80(19), 108148v, 1974; Hydroxylamine Derivatives, Zinner, G. et al.
Chemical Abstracts, vol. 90(25), 203460f, 1979; Dicarbamylhydroxylamine ("isohydroxybiuret"), Zinner, G. et al.
Chemical Abstracts, vol. 114(23), 229316c, 1991; Hydroxamic acid derivatives with potential anti-inflamatory activity, Nagarajan, K. et al.
Chemical Abstracts, vol. 72(21), 110691v, 1970, Zinner, G. et al.
Chemical Abstracts, vol. 108(17), 142964q, 1988, Ho, B. T. et al.
Chemical Abstracts, vol. 73(3), 14048r, 1970, Zinner, G. et al.
W. J. Middleton, "Trifluoroacetonitrile Oxide", J. Org. Chem., 1984, vol. 49, pp. 919-922.
A. K. Saksena et al, "A General Stereocontrolled Route to Carbocyclic C-Nucleosides: (±) Carba-Showdowmycin", Tetrahedron Letters, vol. 22, No. 52, pp. 5227–5230, 1981.
M. Frankel et al, "DL-Cyclocanaline (Cyclohomoserine) and Related Compounds", J. Chem. Soc. (C), 1969.
A. O. Stewart et al, "N,O-Bis(phenoxycarbonyl)hydroxylamine: A New Reagent for the Direct Synthesis of Substituted N-Hydroxyureas", J. Org. Chem., 1992, vol. 57, pp. 5020–5023.

Primary Examiner—José G. Dees
Assistant Examiner—Dwayne C. Jones
Attorney, Agent, or Firm—Irwin M. Stein

[57] ABSTRACT

Describes a process for preparing N,O-disubstituted hydroxylamine compounds comprising reacting an aqueous solution of free hydroxylamine with an equimolar amount of a carbonyl halide-containing compound, e.g., a chloroformate such as phenyl chloroformate, in the presence of a substantially stoichiometric amount of a weak inorganic basic reagent, thereby to produce the N-substituted derivative, and thereafter further reacting an inert organic solvent solution of the N-substituted derivative with an equimolar amount of the corresponding carbonyl halide-containing compound in the presence of a substantially stoichiometric amount of weak inorganic basic reagent, thereby to produce the N,O-disubstituted derivative, e.g., N,O-bis(phenoxycarbonyl) hydroxylamine. In a preferred embodiment, the organic solvent is used also in the reaction that produces the N-substituted derivative. N,O-disubstituted hydroxylamine compounds containing less than 3 weight percent, e.g., less than 0.5 weight percent, of the hydrolysis by-product of the carbonyl halide-containing compound may be produced thereby.

15 Claims, No Drawings

PROCESS FOR PREPARING N,O-DISUBSTITUTED HYDROXYLAMINE COMPOUNDS

DESCRIPTION OF THE INVENTION

The lipoxygenases are a family of enzymes which catalyze the oxygenation of arachidonic acid. The enzyme 5-lipoxygenase converts arachidonic acid to 5-hydroperoxyeicosatetraenoic acid, which is the first step in the metabolic pathway yielding 5-hydroxyeicosatetraenoic acid and leukotrienes. Similarly, 12- and 15-lipoxygenase enzymes convert arachidonic acid to similar products. A variety of biological effects are associated with the products from lipoxygenase metabolism of arachidonic acid and they have been implicated as mediators in various disease states. See, U.S. Pat. No. 4,873,259.

A series of orally active inhibitors of the enzyme, 5-lipoxygenase, which contain the N-hydroxyurea group are described in the aforesaid '259 patent. Inhibitors of 5-lipoxygenase represent a promising therapy for a variety of disorders involving leukotriene mediators.

Stewart et al describes a method for the preparation of substituted N-hydroxyureas by the use of N,O-bis(-phenoxycarbonyl) hydroxylamine. See "N,O-Bis(-phenoxycarbonyl) hydroxylamine; A New Reagent for the Direct Synthesis of Substituted N-hydroxyureas" by Andrew O. Stewart and Dee W. Brooks, J. Org. Chem., 57, pages 5020–5023, 1992. In this article, the authors describe the preparation and reaction of N,O-bis(phenoxycarbonyl) hydroxylamine with alcohols and the conversion of the resultant adduct to N-hydroxyureas.

N,O-bis(phenoxycarbonyl) hydroxylamine is prepared by Stewart et al in an aqueous medium by adding a large stoichiometric excess of phenylchloroformate to free hydroxylamine in the presence of a stoichiometric excess of sodium bicarbonate. The process described by Stewart et al results in the hydrolysis of significant amounts of phenylchloroformate to phenol, which byproduct thereby becomes a contaminant in the N,O-bis(phenoxycarbonyl) hydroxylamine product. When the N,O-bis(phenoxycarbonyl) hydroxylamine product is used to prepare pharmaceutical compounds, removal of the by-product phenol is required. Extensive washing and purification of the phenol-containing hydroxylamine product increases the cost of the product and is economically undesirable from cost and environmental considerations.

SUMMARY OF THE INVENTION

An improved process has now been discovered for preparing N,O-disubstituted hydroxylamine compounds. In a preferred embodiment, N,O-disubstituted hydroxylamine compounds containing less than 3 weight percent of the hydrolysis by-product of the carbonyl halide-containing reactant, e.g., the chloroformate reactant, are prepared. The hydrolysis by-product can be reduced readily to a more acceptable level of less than 0.5 weight percent.

The process of the present invention comprises a chemical reaction that may be staged. In the first stage, free hydroxylamine is reacted with a substantially equimolar amount of a carbonyl halide-containing compound, e.g, a haloformate, in the presence of a stoichiometic amount, or a small stoichiometric excess, of weak inorganic basic reagent, thereby to form the corresponding N-substituted hydroxylamine derivative. Subsequently, in the second stage the N-hydroxylamine derivative produced in the first stage is reacted with a further substantially equimolar amount of the carbonyl halide-containing reactant in a non-reactive (inert) organic solvent and in the presence of a substantially stoichiometric amount of the weak inorganic basic reagent. If desired, the reaction medium can be analyzed at the completion of the addition of the first portion of the carbonyl halide-containing compound to assess the completeness of the reaction in producing the N-substituted hydroxylamine derivative, i.e., to assess the completion of the first stage, before charging the second portion of carbonyl halide-containing compound (second stage). Alternatively, the first and second portions of the carbonyl halide-containing compound may be added slowly and continuously without interruption to the reaction medium provided that the non-reactive solvent and stoichiometric amount of weak inorganic basic reagent are present therein for the second stage.

DETAILED DESCRIPTION OF THE INVENTION

N,O-disubstituted hydroxylamine compounds that may be prepared by the process of the present invention may be represented by one of the following graphic formulae:

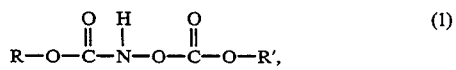

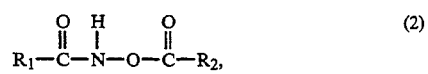

and

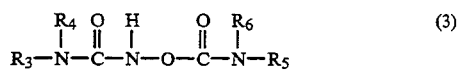

In graphic formula (1), R and R' may each be selected from the group consisting of $C_1$–$C_{12}$ alkyl, $C_1$–$C_{12}$ haloalkyl, $C_6$–$C_{10}$ cycloalkyl, $$(Y)_n\text{-(Ph)}- \text{ and } (Y)_n\text{-(Ph)}(C_1\text{-}C_6)$$

alkyl. The abbreviation Ph represents the phenyl group, Y is a substituent on the aromatic ring of the phenyl group, and n is an integer of from 0 to 3, e.g., 0, 1, or 2. Y may be selected from the group con nitro, cyano and $C_1$–$C_4$ alkyl. When n is 0, the group $$(Y)_n\text{-(Ph)}-$$

is the phenyl group. Typically, not more than two of the Y substituents on the phenyl group are the same. The halo substituent of the $C_1$–$C_{12}$ haloalkyl group or when Y is halo may be selected from fluoro, chloro, bromo, or iodo, more typically fluoro or chloro.

Examples of $C_1$–$C_{12}$ alkyl groups include: methyl, ethyl, propyl, secondary butyl, pentyl, hexyl, tertiary butyl, 2-ethylhexyl, octyl, decyl and dodecyl. The alkyl groups may be branched or straight chain. Examples of $C_1$–$C_{12}$ haloalkyl include: monohaloalkyl or polyhaloalkyl groups, such as chloromethyl, chloroethyl, dichloromethyl, dichloroethyl, trifluoromethyl or trichloromethyl. Examples of $C_6$–$C_{10}$ cycloalkyl groups include: cyclohexyl and 4-tertiary butyl cyclohexyl Examples of

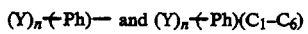

alkyl include: phenyl, chloro-, fluoro-, bromo- or iodophenyl, aminophenyl, aminochlorophenyl, nitrophenyl, nitrochlorophenyl, methylphenyl, dimethylphenyl, cyanophenyl, benzyl, phenylethyl and 4,6-nitro-3-methylphenyl.

More particularly, R and R' in graphic formula (1) are selected from the group consisting of $C_1$–$C_8$ alkyl, e.g., $C_2$–$C_4$ alkyl, $C_2$–$C_8$ haloalkyl, e.g., $C_2$–$C_4$ haloalkyl, cyclohexyl, phenyl and phenyl($C_1$–$C_2$)alkyl, e.g., benzyl.

In graphic formula (2), $R_1$ and $R_2$ may each be selected from the group consisting of $C_1$–$C_{12}$ alkyl, e.g., $C_1$–$C_8$ alkyl such as $C_2$–$C_4$ alkyl, $C_1$–$C_{12}$ haloalkyl, e.g., $C_2$–$C_8$ haloalkyl such as $C_2$–$C_4$ haloalkyl, phenyl and benzyl. Like R and R', the halo groups may be selected from chloro, fluoro, bromo or iodo, preferably chloro or fluoro.

In graphic formula (3), $R_3$, $R_4$, $R_5$ and $R_6$ are each selected from the group consisting of hydrogen, $C_1$–$C_{12}$ alkyl, e.g., $C_1$–$C_8$ alkyl such as $C_2$–$C_4$ alkyl, $C_6$–$C_{10}$ cycloalkyl and phenyl. As used in the descriptions, the term "alkyl" is intended to mean and include both linear and branched chain alkyls and the term "cycloalkyl" is intended to mean and include alkyl-substituted and unsubstituted cycloalkyl groups, e.g., cyclohexyl and tertiary butyl cyclohexyl.

In preparing the N,O-disubstituted hydroxylamine compounds represented by the above-depicted graphic formulae (1)–(3), free hydroxylamine is reacted with a carbonyl halide-containing compound under reaction conditions hereinafter described. Hydroxylamine is commercially available as an acid salt, e.g., hydroxylamine hydrochloride, hydroxylamine sulfate, hydroxylamine phosphate and hydroxylamine-O-sulfonic acid. For the process described herein, hydroxylamine hydrochloride is preferred. The free hydroxylamine is liberated by contacting the hydroxylamine acid salt with a basic reagent, e.g., the weak inorganic basic reagent described hereinafter, in an aqueous medium.

The carbonyl halide-containing compounds that are reacted with hydroxylamine to form the hydroxylamine derivative of formula (1), i.e., the haloformates, may be represented by graphic formulae (4) and (5).

Similarly the carbonyl halide-containing compounds reacted with hydroxylamine to form the hydroxylamine derivative represented by graphic formula (2), i.e., the acyl halides, may be represented by graphic formulae (6) and (7).

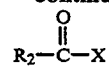

Finally, the carbonyl halide-containing compounds used to prepare the hydroxylamine derivatives represented by graphic formula (3), i.e., the carbamoyl halides, may be represented by graphic formulae (8) and (9).

In graphic formulae (4)–(9), R, R', $R_1$, $R_2$, $R_3$, $R_4$, $R_5$ and $R_6$ are as defined with respect to graphic formulae (1)–(3). X in these graphic formula is halogen, typically chlorine or bromine, preferably chlorine. The carbonyl halide-containing compounds represented by graphic formulae (4)–(9); namely, the haloformates, acyl halides and carbamoyl halides, e.g., chloroformates, acid chlorides and carbamoyl chlorides, are known in the art and may be prepared by procedures well known in the art, if they are not commercially available.

The amount of carbonyl halide-containing compound used in the practice of the present process is in the ratio of about 2 moles of the carbonyl halide compound to 1 mole of free hydroxylamine. When performed as a two-stage process using free hydroxylamine, a substantially equimolar amount of the carbonyl halide compound is used in each stage.

The inorganic basic reagent used in the process described herein should be relatively water-soluble, and have a basicity which is sufficient to neutralize the acidic species, e.g., hydrochloric acid, formed during the reaction, but not so high at the reaction medium pH as to promote hydrolysis of a significant amount of the carbonyl halide-containing compound, e.g., the chloroformate. Stated otherwise, the inorganic basic reagent is preferably a weak hydrolyst, e.g., a material that catalyzes or promotes hydrolysis. The preferred inorganic basic reagents useful in the present process have been termed by those skilled in the art as "weak" basic reagents. Suitable examples of appropriate inorganic basic reagents include the bicarbonates of lithium, sodium and potassium, the carbonates of sodium, lithium and potassium, calcium oxide and magnesium oxide.

Sodium hydroxide and potassium hydroxide may be used as the basic reagent provided that tight pH control of the reaction is observed, i.e., control of the reaction pH at between 8 and 9, to avoid hydrolysis of the carbonyl halide-containing compound. When close control of the reaction pH is not observed, basic reagents like sodium hydroxide have been found to cause excessive hydrolysis of the carbonyl halide-containing compound and therefore are not recommended for use under those conditions. Close control of the reaction pH can be attained by use of commercially available pH controllers, e.g., a pH STAT or a pH controller pump.

The organic solvent used in the process of the present invention should be a liquid at reaction temperatures, capable of dissolving both the intermediate hydroxylamine derivative, i.e., the N-substituted hydroxylamine, and the product, i.e., the N,O-disubstituted hydroxylamine, and have physical properties, e.g., boiling point, that allows it to be readily separated from the product. Moreover, the organic solvent should be chemically non-reactive (chemically inert) with respect to any significant chemical reactivity with the reactants, i.e., the hydroxylamine and carbonyl halide-containing compounds, as well as with the intermediate N-substituted hydroxylamine derivative and the N,O-disubstituted hydroxylamine product. Chemical reactivity includes the formation of complexes with the foregoing intermediate and final products.

In addition, it is preferred that the organic solvent used be one that will not cause environmental difficulties as a result of small amounts being released into the environment, either in vaporous or liquid form, and non-toxic, particularly in the case where the product is used for the preparation of pharmaceutical compounds. Examples of organic solvents that may be used in the process of the present invention include non-halogen containing reagents such as tetrahydrofuran, acetone, acetonitrile, ethyl acetate, toluene, methyl isobutyl ketone and methyl ethyl ketone. Methylene chloride, chlorinated ethylenes, chlorinated benzenes, benzene, dioxane and other such organic solvents may be used but require careful handling to avoid their being released to the environment and careful work-up techniques to avoid residues of the solvent in the product.

The amount of organic solvent used is that amount required to solvate the reaction, i.e., dissolve the intermediate and final product, and is not critical. Economic considerations, the ability to recover and recycle the organic solvent so as to avoid release of the solvent into the atmosphere, separation of the product from the solvent, and environmental concerns are considerations assessed in both choosing the specific organic solvent and the amount of solvent used.

The amount of inorganic basic reagent used in the process of the invention is only that amount (as defined herein) which is required to neutralize the acid by-products generated in the process. Typically, a substantially stoichiometric amount of the inorganic basic reagent is used. However, a slight excess of the basic reagent, e.g., from 1 to 5 molar percent may be employed. In calculating the amount of basic reagent required, any acid by-product generated as the result of the use of the hydroxylamine starting reagent, e.g., hydroxylamine hydrochloride, should be taken into account. For example, the use of 1 mole of hydroxylamine hydrochloride and 2 moles of phenylchloroformate in the preparation of N,O-bisphenoxycarbonyl hydroxylamine will require 3 moles of an inorganic basic reagent, such as sodium bicarbonate. One mole of the basic reagent is required to neutralize the hydrochloric acid associated with the hydroxylamine starting reagent, thereby to generate free hydroxylamine, and 2 moles of the basic reagent is required to neutralize the 2 moles of hydrochloric acid generated by the reaction of 2 moles of phenylchloroformate with tile free hydroxylamine.

The process of the present invention is carried out typically at temperatures of between about 0° and 20° C., e.g., between about 3 and about 15° C., more commonly between about 5° and about 10° C.

In one embodiment of carrying out the process of the present invention, the inorganic basic reagent is dissolved in water and cooled to about 5° C., e.g., with an ice-water bath. The amount of inorganic basic reagent used in this step may be that required only for the generation of the free hydroxylamine, for the generation of the free hydroxylamine and the preparation of the intermediate N-substituted hydroxylamine derivative, or for all of the stoichiometric requirements of the entire process. If less than all of the basic reagent stoichometric requirements is used initially, then additional amount(s) of the basic reagent are added subsequently to the reaction medium prior to the addition of the carbonyl halide-containing compound to the reaction medium. Hydroxylamine acid salt, e.g., hydroxylamine hydrochloride, dissolved in water is added carefully to the solution of the inorganic basic reagent at temperatures typically less than 10° C., e.g., from about 3° to about 5° C. The foregoing step results in the preparation of free hydroxylamine in the aqueous reaction medium.

To the aqueous solution of free hydroxylamine is added carefully in one embodiment ½ (or a substantially equimolar amount, basis the amount of free hydroxylamine) of the total stoichiometric requirements of the carbonyl halide-containing compound, such as the carbonyl halide compound described in graphic formulae (4), (6) or (8), e.g., phenylchloroformate, at temperatures of between about 5° and 9° C., thereby to form the intermediate N-substituted hydroxylamine derivative, e.g., N-phenoxycarbonyl hydroxylamine. The formation of the intermediate occurs readily and is substantially complete when the addition of this amount of the carbonyl halide-containing compound is completed.

If desired, and in a preferred mode of operating, the non-reactive organic solvent may be added prior to the addition of any carbonyl halide-containing compound to the aqueous solution of hydroxylamine. If not added at that time, the non-reactive organic solvent is added to the reaction medium after formation of the N-substituted hydroxylamine derivative, i.e., prior to the addition of the remaining carbonyl halide-containing compound to the reaction medium.

In the second stage, an equimolar amount (basis the intermediate N-substituted hydroxylamine derivative) of carbonyl halide-containing compound, such as the carbonyl halide compound described in graphic formulae (5), (7) or (9), is added carefully to the reaction vessel. The reaction of the intermediate N-substituted hydroxylamine with an additional equimolar amount of the carbonyl halide-containing compound occurs more slowly than the reaction to form the N-substituted derivative. For example, up to 2 hours may be required to complete the second step of the process. Typically, the process of the present invention (first and second stages) may be performed over a total period of from about 1 to about 5 hours, e.g., 1.5–4.5 hours. The addition of the carbonyl halide-containing compound to the reaction medium is regulated to control the temperature of the reaction and avoid the generation of unmanageable amounts of gas, e.g., carbon dioxide, as would be practiced by a prudent chemist or chemical engineer.

Following completion of the addition of all of the carbonyl halide-containing compound to the reaction medium, the product is recovered by conventional techniques. For example, the aqueous (brine) phase may be separated and the organic phase washed with deionized water. The organic solvent may then be removed by stripping on a rotary film evaporator to recover the N,O-disubstituted hydroxylamine product.

In considering the N,O-disubstituted hydroxylamine derivatives of graphic formulae (1), (2) or (3), it is evident that the carbonyl halide-containing compounds of graphic formulae (4) and (5) are used sequentially to prepare the compound of graphic formula (1). Similarly, the carbonyl halide compound of graphic formulae (6) and (7) [and (8) and (9)] are used respectively to prepare the compounds of graphic formulae (2) and (3). The process of the present invention has the flexibility of producing N,O-disubstituted hydroxylamine compounds wherein the N-substituent differs from the O-substituent and wherein the N- and O-substituents are the same. In the latter case, for example, R and R' [in graphic formulae (4) and (5)] are the same, thereby producing an N,O-Bis substituted hydroxylamine. Similarly, $R_1$ and $R_2$ can be the same, $R_3$ and $R_5$ can be the same, and $R_4$ and $R_6$ can be the same. When the N-substituent and O-substituent are different, the present process provides a natural break in the chemical reaction to allow for the addition of the different carbonyl halide-containing compound to the reaction medium containing the intermediate N-substituted hydroxylamine derivative.

The N,O-disubstituted hydroxylamine compounds of graphic formula (1) prepared by the process of the present invention may be used to prepare substituted N-hydroxyureas that may be used in turn to prepare inhibitors of the enzyme 5-lipoxygenase, such as those described in U.S. Pat. No. 4,873,259. The compounds may also be used as intermediates in the synthesis of other organic compounds. For example, N,O-dimethylhydroxylamine is used as an intermediate in the synthesis of herbicides, as described in Belgium Patent 871,762.

The N,O-disubstituted hydroxylamine compounds of graphic formula (2) may be used as an intermediate to make other organic compounds. See, for example, J. Org. Chem., 49, 919–122 (1984) where W. Middleton uses N,O-bis(trifluoroacetyl) hydroxylamine for the synthesis of heterocyclic compounds, and Tetrahedron Letters, Vol. 22, No. 52, 5227-5230 (1981) where A. Saksena et al used this same compound to make a broad spectrum of C-nucleoside antibiotics. N,O-bis(p-chlorobenzoyl) oxyhydroxylamine has been reported as a potential anti-inflammatory agent (Indian J. of Chem., Sect. B, 30B(2), 222–9 (1991)).

The N,O-biscarbamoyl hydroxylamine compounds of graphic formula (3) may be used as an intermediate to make other organic compounds. U.S. Pat. No. 3,192,261 claims such compounds as useful antibacterial agents.

The present invention is more particularly described in the following examples which are intended as illustrative only, since numerous modifications and variation therein will be apparent to those skilled in the art.

EXAMPLE 1

To a 2 liter, 4-necked round bottom reaction flask equipped with a motor driven stirrer, thermometer and addition funnel (with drying tube) was charged 400 milliliters (ml) of distilled water and 264.6 grams (3.15 mole) of sodium bicarbonate. The mixture was stirred and cooled to 5° C. with an ice-water bath. To this aqueous solution, 70.2 grams (99% assay, 1.0 mole) of hydroxylamine hydrochloride dissolved in 100 ml of water was added over 20 minutes while maintaining the temperature of the flask contents at 3° to 5° C.

Ethyl acetate (500 ml) was then added to the reaction flask, followed by the dropwise addition over 35 minutes of 156.7 grams (1.0 mole) of phenylchloroformate. The temperature of the flask contents was maintained at 5° to 9° C. during the addition of the phenylchloroformate. The resultant reaction mixture was found to contain by HPLC analysis (area percent) 94.5 percent N-phenoxycarbonyl hydroxylamine, 1.9 percent phenol and 3.5 percent N,O-bisphenoxy-carbonyl hydroxylamine.

An additional 1.56.7 grams (1.0 mole) of phenylchloroformate was then added dropwise to the reaction mixture over 35 minutes and the reaction mixture stirred for an additional 2 hours. HPLC analysis (area percent) of the product mixture showed it to contain 93.2 percent N,O-bisphenoxycarbonyl hydroxylamine, 2.0 percent N-phenoxycarbonyl hydroxylamine and 1.5 percent phenol.

The contents of the reaction flask (at 13° C.) were transferred to a separatory funnel and the slightly hazy brine phase separated. The clear ethyl acetate phase was washed with 200 ml of deionized water while gently mixing the organic phase. Ethyl acetate was removed by stripping on a rotary film evaporator at 100 mm (Hg) of vacuum initially. A final stripping at 10 to 20 mm (Hg) vacuum gave 274 grams of a slightly yellow oil. HPLC analysis (area percent) of the product found it to contain 94.6 percent N,O-bisphenoxycarbonyl hydroxylamine, 2.4 percent phenol and 1.26 percent of N-phenoxycarbonyl hydroxylamine.

The yellow oil product was mixed with 200 ml of methanol and 200 ml of water in a beaker and the mixture homogenized with a Janke & Kunkel AG homogenizer (Type SD 45, Model 8479) to give N,O-bisphenoxycarbonyl hydroxylamine as a lumpy solid. HPLC analysis (area percent) of the product found it to contain 95.7 percent N,O-bisphenoxycarbonyl hydroxylamine, 1.8 percent phenol and 0.63 N-phenoxycarbonyl hydroxylamine. The solid product was rehomogenized in 200 ml of water for 5 minutes to produce finer granules of solid product and this product was found by HPLC analysis (area percent) to contain 97.9 percent of N,O-bisphenoxycarbonyl hydroxylamine, 0.38 percent phenol and 1.7 percent N-phenoxycarbonyl hydroxylamine. This product was placed in a vacuum oven at 50°–55° C. The dried product was a white fluffy powder containing 98.5 percent of the N,O-bisphenoxycarbonyl hydroxylamine and a trace of phenol. The yield of product was 88.7 percent based on hydroxylamine.

EXAMPLE 2

Following the procedure of Example 1, 264.6 grams (3.15 mole) of sodium bicarbonate and 400 ml of distilled water were charged to the 2-liter reaction flask and cooled to 3° C. with an ice-acetone bath. Hydroxylamine hydrochloride (70.2 grams, 1.0 mole, 99% assay) was added to 100 ml of distilled water in a separate flask and dissolved in the water by the application of warm tap water to the flask. The hydroxylamine hydrochloride aqueous solution was added to the reaction flask over 15 minutes and stirred for an additional 15 minutes. The temperature of the reaction flask was about −3° C.

Phenylchloroformate (156.6 grams, 1.0 mole) was added slowly to the reaction flask over 30 minutes during which time the temperature in tile flask was maintained between −3° C. and 7° C. A sample of the reaction mixture was taken and analyzed by HPLC. Results (area percent) showed the sample to contain 59.7 percent N-phenoxycarbonyl hydroxylamine, 19.2 percent phenol and 21.1 percent N,O-bisphenoxycarbonyl hydroxylamine.

Ethyl acetate (500 ml) was added to the reaction flask and stirred. With the temperature of the reaction mixture at 2° C. 156.6 grams (1.0 mole) of phenylchloroformate was added slowly to the reaction flask over 30 minutes. Thereafter, the reaction mixture was stirred until phenylchloroformate was not detected in the organic phase (about 3 hours). A sample of the organic phase was analyzed by HPLC and found to contain (area percent) 81.1 percent N,O-bisphenoxycarbonyl hydroxylamine, 1.2 percent N-phenoxycarbonyl hydroxylamine and 10.8 percent phenol.

COMPARATIVE EXAMPLE

The procedure for preparing N,O-Bis(phenoxycarbonyl) hydroxylamine described in A. Stewart's article (J. Org. Chem., 57, 5020–5023 (1992)) is followed in this comparative example.

To a 2-liter, 4-necked round bottom reaction flask equipped with a motor driven stirrer, thermometer and addition funnel was added 500 ml of water and 71.5 grams (0.85 mole) of sodium bicarbonate. The solution was cooled to 0° C. with an acetone-ice bath. Hydroxylamine hydrochloride (29.4 grams, 0.42 mole) was added slowly to the reaction flask over 15 minutes followed by stirring for 45 minutes. Phenylchloroformate (200 grams, 1.28 mole) was charged slowly to the reaction flask over 30 minutes followed by the addition of a cold (0° C.) solution of 107.3 grams (1.28 mole) of sodium bicarbonate in one liter of water. The reaction mixture was then stirred for an additional 30 minutes at 0° C. The acetone-ice bath was removed and replaced with a warm water bath to bring the reaction mixture to room temperature (23° C.). The reaction mixture was then stirred while at room temperature for 2 hours. White solids were observed in the reaction mixture.

The suspension in the reaction flask was filtered, but most of the solids stayed in the reactor adhering to the reactor wall. Water (500 ml) was added to the reactor to dislodge the solids without success. Hexane (400 ml) was added to the flask and stirred for 15 minutes to dislodge the solids, which were then filtered and washed twice with 400 ml of hexane. HPLC analysis (area percent) of the solids showed it to contain 77.9 percent N,O-bisphenoxycarbonyl hydroxylamine, 4.7 percent phenol, and 2.63 percent phenylchloroformate (14.8%, unknowns).

The results for this comparative example show that a high level of unknown product is formed in this process, and that some phenylchloroformate remains unreacted.

Although the present invention has been described with reference to the specific details of certain embodiments thereof, it is not intended that such details should be regarded as limitations upon the scope of the invention except as and to the extent that they are included in the accompanying claims.

We claim:

1. A process for preparing an N,O-disubstituted hydroxylamine representable by the following graphic formula,

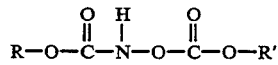

comprising, in combination, the steps of:
(a) reacting hydroxylamine with a substantially equimolar amount of a haloformate representable by the following graphic formula,

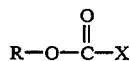

in the presence of a substantially stoichiometric amount of a water-soluble, weak inorganic basic reagent, thereby to form the corresponding N-substituted hydroxylamine derivative,
(b) reacting said N-substituted hydroxylamine derivative in a non-reactive organic solvent with a substantially equimolar amount of a haloformate representable by the following graphic formula,

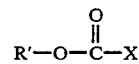

in the presence of a substantially stoichiometric amount of said weak inorganic basic reagent, said reactions being performed at temperatures of from about 0° C. to about 20° C., thereby to form the corresponding N,O-disubstituted hydroxylamine derivative, wherein
(i) R and R' are each selected from the group consisting of $C_1$-$C_{12}$ alkyl, $C_1$-$C_{12}$ haloalkyl, $C_6$-$C_{10}$ cycloalkyl, $(Y)_n$—Ph) and $(Y)_n$—Ph)($C_1$-$C_6$) alkyl, said Ph being phenyl, Y is a substituent on said phenyl ring, each Y is selected from the group consisting of halo, amino, nitro, cyano, and $C_1$-$C_4$ alkyl, and n is an integer of from 0 to 3, provided that not more than 2 of such Y groups are the same, and
(ii) X is halogen.

2. The process of claim 1 wherein R and R' are the same and X is chlorine.

3. The process of claim 2 wherein the weak inorganic base is sodium bicarbonate.

4. The process of claim 3 wherein the non-reactive organic solvent is ethyl acetate or tetrahydrofuran.

5. The process of claim 2 wherein R and R' are each selected from $C_1$-$C_8$ alkyl, $C_2$-$C_8$ haloalkyl, phenyl or benzyl.

6. The process of claim 5 wherein the weak inorganic base is sodium bicarbonate and the non-reactive organic solvent is ethyl acetate or tetrahydrofuran.

7. The process of claim 1 wherein step (a) of the process is performed also in the presence of the non-reactive organic solvent.

8. The process of claim 7 wherein R and R' are the same, X is chlorine, and the weak inorganic base is sodium bicarbonate.

9. The process of claim 8 wherein R and R' are phenyl.

10. The process of claim 9 wherein the organic solvent containing the N,O-disubstituted hydroxylamine derivative product is washed with water, and the organic solvent removed, thereby to provide a product having less than 0.5 weight percent of the hydrolysis by-product of the haloformate.

11. The process of claim 9 wherein the organic solvent is ethyl acetate or tetrahydrofuran.

12. The process of claim 1 wherein R and R' are each selected from the group consisting of $C_1$-$C_8$ alkyl, $C_2$-$C_8$ haloalkyl and $(Y)_n$(Ph), said Ph being phenyl, Y is selected from halo, nitro and $C_1$-$C_4$ alkyl, and n is the integer 0 or 1; and X is chlorine.

13. The process of claim 12 wherein R and R' are the same.

14. The process of claim 13 wherein step (a) is performed also in the presence of the non-reactive organic solvent.

15. The process of claim 14 wherein the inorganic basic reagent is sodium bicarbonate, and the organic solvent is selected from the group consisting of ethyl acetate and tetrahydrofuran.

* * * * *